United States Patent [19]

Kibler et al.

[11] Patent Number: 5,005,430

[45] Date of Patent: Apr. 9, 1991

[54] AUTOMATED MEMBRANE FILTER SAMPLER

[75] Inventors: Jack M. Kibler, Minerva; Jack K. Schmotzer, Alliance; Charles C. Stauffer, Beloit, all of Ohio

[73] Assignee: Electric Power Research Institute, Inc., Palo Alto, Calif.

[21] Appl. No.: 463,047

[22] Filed: Jan. 11, 1990

Related U.S. Application Data

[63] Continuation of Ser. No. 355,147, May 16, 1989, abandoned, which is a continuation of Ser. No. 113,780, Oct. 26, 1987, abandoned.

[51] Int. Cl.$^5$ ............................................. G01N 1/16
[52] U.S. Cl. ............................... 73/863.01; 73/863.33
[58] Field of Search ............ 73/863.01, 863.21, 863.23, 73/863.25, 863.31, 863.33, 863.41, 863.61, 864.73, 61 R; 137/625.11; 422/62, 81; 210/662

[56] References Cited

U.S. PATENT DOCUMENTS

| | | | |
|---|---|---|---|
| 3,681,997 | 8/1972 | Allen et al. | 73/863.61 |
| 4,341,124 | 7/1982 | Rodgers et al. | 73/863.01 |
| 4,414,858 | 11/1983 | Peterson et al. | 73/863.33 |
| 4,472,354 | 9/1984 | Passell et al. | 436/38 |
| 4,481,833 | 11/1984 | Bajek | 73/863.41 |
| 4,496,286 | 1/1985 | Gagnon | 73/862.35 |
| 4,608,159 | 8/1986 | Collins, Jr. | 210/101 |

OTHER PUBLICATIONS

Scanivalve Corp. Publications.
Scanivalve Applications-Bulletin No. SA2-Measuring Fluid Inventory in Storage Tanks-2 pages.
Scanivalve Applications-SA3-Measuring Fluid Flow Across Orifice Plates-1 page (Mar. 1977).
Scanivalve Applications-SA4-Adhesive Bonding Autoclave Vacuum Monitor-1 page (May 1985).
Scanivalve Applications-SA5-3-15 PSI Monitor for Process Control-1 page (Feb. 1980).
Scanivalve Applications-Bulletin No. SA8-Samplivalve-1 page.
Scanivalve Applications-SA11-Measuring Movement of Water in Unsaturated Soil-1 page (Sep. 1977).
Scanivalve Applications-SA15-Calibrating Multiple Instruments with Multiple Calibrate Pressures-1 page (Jan. 1977).
Scanivalve Technotes-ST2-Internal Duct Flow Measurements-1 page (Jun. 1970).
Scanivalve Technotes-Bulletin No. ST4-Serial Random Access with Rotary Solenoid Drives-1 page (©1976).
Scanivalve Technotes-Bulletin No. ST5-Differential Pressure Pairs-1 page (©1972).
Scanivalve Technotes-Bulletin No. ST9-Minimizing Volume of Pressure Transducer By Oil Filling-1 page (©1976).
Scanivalve Technotes-ST13-Satellite Configuration For Fluid Switch Wafers-1 page (Mar. 1977).
Some Typical Scanivalve Applications-SA Nos. 2,3,5,6,8-13 and ST No. 7-1 page (©1975).
Scanivalve Corp.-D-500 PSI Applications-1 page (copyright 1977).
Interim Concensus Guidelines on Fossil Plant Cycle Chemistry-CS-4629-Research Project 2712-1-Final Report, Jun. 1986, prepared by Sargent & Lundy for Electric Power Research Institute-Principal Investigators: A. F. Aschoff, Y. H. Lee, D. M. Sopocy and O. Jonas (Jonas, Inc.)-Rept. Summary (2 pages), Title Page (1 page), Abstract (p. iii), Summary (pp. S-1 thru S-6), Appendix B-Representative Sampling (p. B-1 thru B-3).

*Primary Examiner*—Robert Raevis
*Attorney, Agent, or Firm*—Robert J. Edwards; Vytas R. Matas; Eric Marich

[57] ABSTRACT

An apparatus for simultaneously acquiring a plurality of samples of ionic and particulate impurities from a fluid stream by means of a plurality of filter pairs.

2 Claims, 1 Drawing Sheet

Sentry Equipment Corp.-Product Brochures/Literature.
E-31-03-Model VREL-Variable Pressure Reducing Element-2 pages (5/79).
Sample Cooler-TF Series-2 pages (1/1/73).
Aschoff et al., "Monitoring Cycle Chemistry at Six Fossil Plants", 47th Annual Meeting Int'l. Water Conference, Pitt., Pa., Oct. 27-29, 1986.
Guideline Manual on Instrumentation and Control for Fossil Plant Cycle Chemistry-Research Project 2712-2-Final Draft Report, Dec. 1986-Prepared by Sheppard T. Powell Associates for Electric Power Research Institute-Principal Investigators: R. D. Hopkins, E. H. Hull and K. J. Shields-Project Manager: S. Yorgiadis-Title Page (1 page), Abstract (p. iii), Summary (p. S-1 thru S-5), Section 2-Sampling and Sample Conditioning (pp. 2-1, 2-2; 2-47 thru 2-54; and 2-63 thru 2-73), Section 6-Operational Considerations (pp. 6-1, 6-2), Section 8-Research Requirements to Advance the State of the Art (pp. 8-1 and 8-5 thru 8-9).
Water Chemistry Control For Power Plants-W. A. Nestel, K. A. Selby, L. E. Eater and R. M. Ricker--Power Engineering Magazine-Apr. 1980-pp. 92 thru 95.

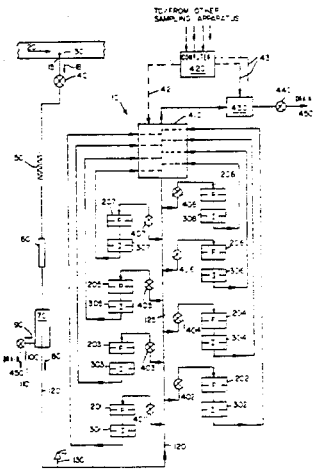

AUTOMATED MEMBRANE FILTER SAMPLER

This is a continuation of application Ser. No. 07/355,147, Filed May 16, 1989, which is a continuation of application Ser. No. 07/113,780, Filed Oct. 26, 1987, now abandoned.

BACKGROUND OF THE INVENTION

1. Field of the Invention

This invention relates to fluid sampling systems, and more particularly to an automatic water sampling apparatus and method for rapidly and simultaneously collecting a large number of ionic and particulate samples from process streams in boiler systems.

2. Description of the Prior Art

Impurities in water systems exist primarily in two forms, particulate and ionic. In many cases, it is necessary to measure both the level of particulates and the level of ionic species present in water systems. Particulate impurities can be sampled through the use of membrane filters. Depending on the size of the the particles present in the water system, a membrane filter of appropriate pore size is selected. As a sample of the water stream is passed through the membrane filter, the particulate impurities collect on the membrane. During this sampling process, the volume of water passed through the filter is measured. The membrane filter containing the particulate impurities is removed and returned to the laboratory where measurements are made of the amount of particulate impurities present on the membrane. The concentration of the particulate impurities in the water system is then determined by dividing the amount of particulate impurities collected on the membrane by the total water volume throughput.

In a similar manner, ionic impurities can be collected on an ion exchange resin impregnated membrane or in a column of ion exchange resin. As a water sample containing ionic impurities passes through the ion exchange resin impregnated membrane, the ionic impurities are collected on the resin. As with the case of collection of particulate samples, the volume of water passed through the membrane is measured. The membrane is returned to the laboratory where measurements for the amount of ionic impurities are conducted. The concentration of ionic impurities is then determined by dividing the amount of ionic impurities collected on the resin by the total volume throughput.

Frequently these types of sample collection media are used in combination in water sampling systems. This is usually accomplished by first passing the water stream through the membrane filter (to remove particulates) and then immediately through an ion exchange resin impregnated membrane a column of ion exchange resin (to remove ionic impurities). A typical application of such a sampling system is for the collection of corrosion products in condensate/feedwater systems of power plants.

A typical sampling apparatus for the collection of particulate and ionic impurities consists of a sample line connected to a filter holder containing a membrane filter, followed by a second filter holder containing ion exchange resin impregnated membranes. This in turn is connected to either a flowrator (for measurement of flowrate vs. time) or to a flow totalizer (for measurement of total water volume throughput). A bypass line is usually provided upstream of the first filter holder and valves are located in the bypass line immediately upstream of the first filter holder and immediately downstream of the second filter holder. When sampling is to occur, the flow of sample water is initiated through the sample line and out the bypass line of the sample apparatus.

Once the filter holders have been loaded with the appropriate type of membranes, the valves upstream and downstream of the filter holders are opened and the bypass valve is partially closed to provide sample flow through the filter holders. The volume of water passed through the filters is measured using the above flow measuring devices.

Operation of the system is completely manual, however, and the collection of samples must be interrupted each time that the membrane filters require changing. Oftentimes it is desirable to collect membrane samples from several locations in a water system simultaneously over short periods of time, especially during transient conditions. In such situations the use of a manual sampling apparatus, such as that previously described, is not practical. Such an operation would be very labor intensive, as well as very difficult to coordinate, since the particular times at which samples are be obtained, the length of time that a sample is to be collected, and the time interval between samples may be critical to the data desired.

Water sampling systems for ionic impurities are known, e.g. U.S. Pat. No. 4,414,858 (Peterson, et al). This system and others as found in U.S. Pat. Nos. 4,472,354 (Passell, et al) and 4,608,159 (Collins, Jr.) typically also use filters to remove particulates from the sample stream.

It has thus become desirable to develop an apparatus and method capable of collecting membrane samples from several locations in a fluid system simultaneously over short periods of time that does not require a significant amount of manpower and yet provides for sampling capability that can accommodate transient changes of a rapid nature.

SUMMARY OF THE INVENTION

The present invention provides an automatically controlled apparatus for collecting a plurality of samples of particulate and ionic impurities from a fluid stream.

Accordingly, one aspect of the present invention is drawn to an apparatus for collecting a plurality of samples of particulate and ionic impurities from a fluid stream by means of a plurality of pairs of filters for removing particulate and ionic impurities. Each pair of filters can be individually isolated and automatic valve means are used to direct flow from a sample line connected to the fluid stream in any desired sequence to each of the pairs of filters, and for any desired length of time. A computer and flow measurement means determine the flow rate and total flow of fluid through each of the filter pairs, as well as the sequence in which flow through each of the filter pairs occurs.

Another aspect of the present invention is drawn to a method for collecting samples of ionic and particulate impurities from a fluid stream from a plurality of pairs of filters. The steps in this method include: providing samples of fluid from the fluid stream; conveying the samples to a plurality of filter holder pairs; directing the samples through the filter holder pairs in a predetermined sequence and for a predetermined period of time; removing the particulate impurities from the samples; removing the ionic impurities from the samples; and measuring the flow rate and total flow of fluid through each pair of filters and calculating the total volume sampled by each of the pairs of filters.

The various features of novelty which characterize the invention are pointed out with particularity in the claims annexed to and forming a part of this disclosure. For a better understanding of the invention, and the operating advantages attained by its use, reference is made to the accompanying drawing and descriptive matter in which a preferred embodiment of the invention is illustrated.

DESCRIPTION OF THE PREFERRED EMBODIMENTS

Figure 1:
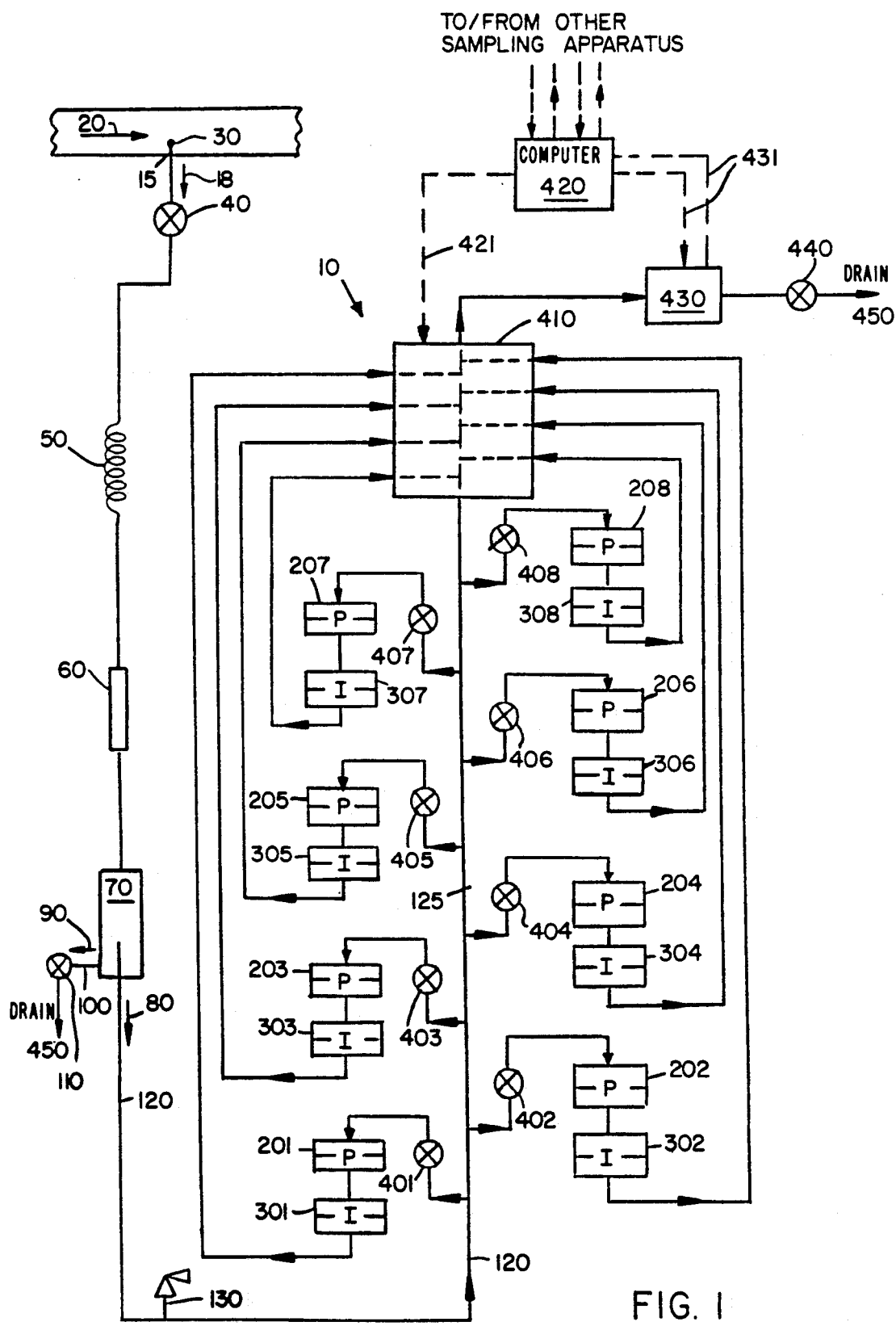
FIG. 1 is a schematic diagram illustrating the preferred embodiment of the present invention.

The present invention may require certain details for a clear understanding of its unique aspects and applications which details may not be apparent to certain individuals not too familiar with the present art from a reading of the present specification. If this is the case, the reader is referred to a paper presented at the 47th Annual Meeting—International Water Conference, held at Pittsburgh, Pennsylvania on Oct. 27-29, 1986, entitled "EPRI RP2712-3 Monitoring Cycle Chemistry at Six Fossil Plants" presented by A. F. Aschoff, D. M. Sopocy, C. C. Stauffer and R. B. Dooley. It is the intention of the Applicants to include the material from this paper into the present specification and this material is therefore incorporated by reference herein and appears in the file history by virtue of it being filed in the U.S. Patent Office with the present specification.

Referring now to FIG. 1, there is shown a sampling apparatus 10 according to the present invention connected at a single location 15 of a process stream 20. In practice, it is anticipated that several sampling apparatus 10 would be employed in a typical power plant, each arranged to monitor a given process stream 20. In operation, a fluid sample 18 is removed from the process stream 20, through a properly-engineered sampling nozzle 30. For an example of specific design requirements for such a sampling nozzle 30, the reader is referred to A.S.T.M. methods D-1192 and D-3370, Section 11, Volume 11.01. The fluid sample 18 then passes through an isolation valve 40.

Where sample conditioning is needed, the fluid sample 18 passes through a rough cooler 50, and is depressurized to about 50 psi, preferably using a variable capillary pressure reducing element 60. Rough cooling and depressurization are advantageously done as close to the sample point 15 as possible.

A sample splitter 70, preferably an isokinetic tee, splits the fluid sample 18 into a first sample stream 80, and a second sample stream 90 which passes through a bypass line 100 having a control valve 110. The sample splitter 70 allows a portion of the flow to be obtained for "grab" samples or other chemistry monitoring systems. The control valve 110 is used to control the amount of flow bypassing the sampling apparatus 10, and thus permits large volumes of flow to pass through the sampling conditioning equipment 50, 60 resulting in a more representative fluid being present in the sample streams 80, 90.

The sample stream 80 next passes through a sample line 120 having a relief valve 130, to prevent overpressurizing the sampling system. The sample line 120 is connected to a manifold system 125 of filter holders. In the preferred embodiment shown in FIG. 1, the sampling apparatus 10 comprises eight pairs of filter holders 201-208 and 301-308. Filter holders 201-208 contain particulate membrane filters P which remove particulate impurities from the sample stream 80. Any type of particulate-removing membrane filter P would be acceptable. Filter holders 301-308, located downstream of filter holders 201-208, respectively, contain cation resin membranes I for collecting ionic impurities. In the preferred embodiment, eight pairs of membrane filter P and cation resin membranes I are used for sampling under computer control, before operator intervention is required, as will be described herein. It is necessary to locate the membrane filters P upstream of the cation resin membranes I in order to separate the particulates from the ionic impurities, before collecting the ionic impurities. This is because particulates tend to coat over the ion exchange sites, inhibiting the collection efficiency of the cation resin membranes; as such, it is preferred to remove the particulates first, prior to ionic removal.

Each particulate—ionic membrane filter holder pair 201-208/301-308 is preceded by a corresponding isolation valve 401-408. These isolation valves 401-408 are used to shut off flow to individual filter holder pairs 201-208/301-308 so that the particulate P and cation resin I membranes can be changed on an individual filter holder pair (e.g. 201/301) without diverting flow from the entire sampling apparatus 10.

The effluent of each set of filter holder pairs 201-208/301-308 is connected to an automatic valve device 410. The position of this valve device 410 is controlled by a computer 420, over line 421. The computer 420 is programmed by the operator. The computer 420 can be preprogrammed to control the automatic valve device 410 to allow the sample stream 80 to flow through some, all or none of the filter holder pairs 201-208/301-308, in any chosen sequence, and to allow the sample stream 80 to flow for any length of time through a given filter holder pair. The computer 420 can also select the time interval between flow occuring in one filter holder pair 201-208/301-308 and the flow occuring in another filter holder pair 201-208/301-308. The automatic valve device 410 can be set such that the sample stream 80 bypasses all of the filter holder pairs 201-208, 301-308, or may be set to allow flow through any one of the individual filter holder pairs 201-208/3-01-308.

The automatic valve device 410 is preferably a Samplivalve automatic valve device sold by Scanivalve Corporation. The application of the Samplivalve as the automatic valve device 410 in the present invention is different from the intended application envisioned for a Samplivalve.

Normally, a Samplivalve is connected such that it receives a single sample stream and then distributes that stream to one of as many as twelve different effluent ports on the Samplivalve. In the present invention, however, when a Samplivalve is used as the automatic valve device 410, the Samplivalve is connected such that it can receive a flowing stream from up to twelve different filter holder pairs 201-208/301-308 (and others not shown) and direct it out of a single effluent port on the Samplivalve. The operation of the Samplivalve is such that flow of the sample stream 80 is permitted through only one of the up to twelve filter holder pairs 201-208/301-308 (and others not shown) at a time, while flow to the remaining filter holder pairs 201-208/301-308 (and other not shown) is prevented. In practice however, up to eleven filter holder pairs 201-208/301-308 (and others not shown) and one bypass line (not shown) may be connected to the Samplivalve when used as the automatic valve device 410. The filter holder pairs 201-208/301-308 are connected in a specific order to the Samplivalve, taking advantage of the operation of the Samplivalve in that the opening of each of the ports therein occurs in a specific order with the Samplivalve switching in sequence to the next port when it receives a signal from the computer 420. Because of this special sequencing order of the Samplivalve, it is necessary to connect the effluent of the filter holder pairs 201-208/301-308 and the bypass line (not shown) beginning with the bypass line (not shown) connected to the first position (otherwise called the home position), filter holder pair 201/301 connected to the second position, filter holder pair 202/302 connected to the third position, and so on through the last filter holder pair 208/308.

It is also necessary to assemble the filter holder pairs 201-208/301-308 and manifold 125 in a vertical orientation as shown in FIG. 1. The direction of flow of sample stream 80 into the sampling apparatus 10 must be in an upward direction with sequencing of the filter holders 201-208/301-308 beginning with filter holder pair 201/301, followed by filter holder pair 202/302 and so on. The upward flow of the sample stream 80, the vertical orientation of the manifold 125 and the sequencing of the filter holder pairs 201-208/301-308 in the specified order minimize the possibility of deposition of particulates within the manifold 125 and contamination of subsequent filter holder pairs 201-208/301-308. This allows for collection of the most representative sample from the sample stream 80 as possible.

Flow measurement means 430, for measuring the flow rate of the sample fluid through each of the filter pairs 201-208/301-308 is fluidically connected downstream of the automatic valve device 410 and provides flow rate data which is provided to the computer 420 over lines 431. The computer 420 integrates the flow rate data with respect to time to determine the total volume sampled by each of the filter holder pairs 201-208/301-308 during the sampling period. The flow rate means 430 can be of any known type, and is, advantageously, a turbine meter.

A control valve 440, located downstream of the flow rate means 430, is used to set the required flow rate of the sample fluid 80 through the filter holder pair 201-208/301 308 and exhausts the sample fluid 80 to a drain 450. The computer 420 functions to control the sequencing of the automatic valve device 410 such that flow to each filter holder pair 201-208/301-308 is initiated and stopped at the appropriate pre-programmed time, receives flow rate data from flow measurement means 430 versus time for each filter holder pair, 201-208/301-308, integrates the flow rate data with respect to time to determine the total volume sampled by each filter holder pair 201-208/301-308, and stores the values of sample volume, start time and stop time data in a data base. The computer 420 can be programmed to begin sample flow to a specific filter holder pair 201-208/301-308 at a specified time and stop sample flow to a filter holder pair 201-208/301-308 at a specified time such that the samples are collected in series over a predetermined period of time. The computer 420 can be programmed such that the samples are collected one right after the other, with no appreciable time intervals therebetween, or such that there are time intervals between samples during which no samples are collected.

After the collection of particulates and ionic impurities on the membrane filters P and cation resin membranes I is complete, the membrane filters P and cation resin membranes I are manually removed from the filter holder pair 201-208/301-308 and new membranes and cation resin membranes P, I are placed in the filter holder pairs 201-208/301-308. The collected samples are transported to the laboratory and analyzed by conventional chemical analysis methods. As such, the present invention is drawn to the automatic collection of particulate and ionic impurities, per se, and not to any later analysis that could be performed on the membrane filters P and cation resin membrane I for the amounts of the impurities.

While a specific embodiment of the present invention has been shown and described in detail to illustrate the application of the principles of the invention, certain modification and improvements will occur to those skilled in the art upon reading the foregoing description. For example, and with reference to the embodiment shown in FIG. 1, several of the automated sampling apparatus 10 described in FIG. 1 can be installed in an operating fluid system such as a power plant such that a series of samples collected on membrane filter P and cation resin membranes I can be collected from several locations within the operating fluid system simultaneously. All of these sampling apparatus 10 devices can be controlled by the single central computer 420. The number of automated sampling apparatus 10 employed is only limited by the capacity of the central computer 420. It is thus understood that the details of all such modifications and improvements have been deleted herein for the sake of conciseness and readability but are properly within the scope of the following claims.

We claim:

1. An apparatus for collecting samples of ionic and particulate impurities from a fluid stream, comprising:

a sample line connected to said fluid stream;

a vertical manifold, fluidically connected to said sample line, for upwardly conveying a sample stream taken from said fluid stream to a plurality of filter holder pairs, each filter holder pair having a first filter holder removably securing a first filter for removing particulate impurities from said sample stream and a second filter holder, located downstream of said first filter holder, for removably securing a second filter for removing ionic impurities from said sample stream;

a plurality of isolation valves, located between said manifold and each of said filter holder pairs, for fluidically isolating each of said filter holder pairs from said manifold;

a single automatic valve device, fluidically connected to and downstream of said manifold and each of said filter holder pairs, for permitting the flow of said sample stream through only one of said plurality of filter holder pairs at a time while preventing flow to the remaining filter holder pairs;

means for determining the flow rate of said sample stream through each of said filter holder pairs; and a computer, connected to said single automatic valve device and to said means for determining the flow rate of said sample stream, for controlling the single automatic valve device to allow said sample stream to flow through each of said plurality of filter holder pairs, in a desired sequence, for a desired length of time through each filter holder pair, and with a desired time interval between flow occurring in one filter holder pair and flow occurring in another filter holder pair, and for determining the total volume of sample stream sampled by each filter holder pair.

2. An apparatus for collecting samples of ionic and particulate impurities from a fluid stream as recited in claim 1, wherein said single automatic valve device is a Samplivalve connected such that it can receive a flowing stream from each of said filter holder pairs and direct it out of a single effluent port on the Samplivalve.

* * * * *